US006879850B2

United States Patent
Kimball

(10) Patent No.: US 6,879,850 B2
(45) Date of Patent: Apr. 12, 2005

(54) PULSE OXIMETER WITH MOTION DETECTION

(75) Inventor: Victor E. Kimball, Burnsville, MN (US)

(73) Assignee: Optical Sensors Incorporated, Eden Prairie, MN (US)

( * ) Notice: Subject to any disclaimer, the term of this patent is extended or adjusted under 35 U.S.C. 154(b) by 19 days.

(21) Appl. No.: 10/222,616

(22) Filed: Aug. 16, 2002

(65) Prior Publication Data

US 2004/0034293 A1 Feb. 19, 2004

(51) Int. Cl.$^7$ ................................................ A61B 5/00
(52) U.S. Cl. ....................................................... 600/336
(58) Field of Search ................................. 600/310, 322, 600/323, 330, 336

(56) References Cited

U.S. PATENT DOCUMENTS

| | | | |
|---|---|---|---|
| 4,802,486 A | | 2/1989 | Goodman et al. |
| 5,025,791 A | * | 6/1991 | Niwa .......................... 600/483 |
| 5,178,154 A | | 1/1993 | Ackmann et al. |
| 5,226,417 A | * | 7/1993 | Swedlow et al. ........... 600/336 |
| 5,337,744 A | | 8/1994 | Branigan |
| 5,485,847 A | | 1/1996 | Baker, Jr. |
| 5,502,558 A | | 3/1996 | Menders et al. |
| 5,505,199 A | | 4/1996 | Kim |
| 5,587,785 A | | 12/1996 | Kato et al. |
| 5,662,106 A | | 9/1997 | Swedlow et al. |
| 5,743,263 A | | 4/1998 | Baker, Jr. |
| 6,018,673 A | | 1/2000 | Chin et al. |
| 6,058,331 A | | 5/2000 | King |
| 6,181,959 B1 | | 1/2001 | Schöllermann et al. |
| 6,272,363 B1 | | 8/2001 | Casciani et al. |
| 6,334,065 B1 | | 12/2001 | Al-Ali et al. |
| 2004/0010185 A1 | * | 1/2004 | Kimball et al. ............. 600/310 |
| 2004/0034294 A1 | * | 2/2004 | Kimball et al. ............. 600/323 |

OTHER PUBLICATIONS

Webster's New World Dictionary, Third College Edition, Simon & Schuster, Inc., 1988, p. 1223.*

* cited by examiner

Primary Examiner—Eric F. Winakur
(74) Attorney, Agent, or Firm—Oppenheimer Wolff & Donnelly LLP; Barbara A. Wrigley

(57) ABSTRACT

There is a need for a technique to compensate for, or eliminate, motion-induced artifacts in patient-attached critical care monitoring instruments. Consequently, the invention is directed to improving pulse-oximetry by incorporating additional signals to aid in the triggering of the pulse-oximeter or in analyzing the data received by the pulse oximeter. This includes detecting when the patient moves and analyzing the pulse-oximetry data in light of the detected movement.

29 Claims, 14 Drawing Sheets

| POD$_i$ | t$_i$ |
|---|---|
| POD$_1$ | t$_1$ |
| POD$_2$ | t$_2$ |
| POD$_3$ | t$_3$ |
| POD$_4$ | t$_4$ |
| POD$_5$ | t$_5$ |
| ... | ... |
| ... | ... |

| PMD$_j$ | tt$_j$ |
|---|---|
| PMD$_1$ | tt$_1$ |
| PMD$_2$ | tt$_2$ |
| PMD$_3$ | tt$_3$ |
| PMD$_4$ | tt$_4$ |
| PMD$_5$ | tt$_5$ |
| ... | ... |
| ... | ... |

FIG. 9

PULSE OXIMETER WITH MOTION DETECTION

This application is related to "Improved Pulse Oximeter", filed on even date herewith by V. E. Kimball and P. LaPlante, having attorney docket no. 1535.4US01, which is incorporated herein by reference.

FIELD OF THE INVENTION

The present invention is directed generally to medical devices and more particularly to non-invasive optical sensors for physiologic parameters such as blood oxygen saturation content.

BACKGROUND

Optical spectroscopy techniques have been developed for a wide variety of uses within the medical community. For example, pulse oximetry and capnography instruments are in widespread use at hospitals, both in the surgery suites and the post-op ICU's. These technologies have historically been based on absorption-based spectroscopy techniques and have typically been used as trend monitors in critical care environments where it is necessary to quickly determine if a patient's vital parameters are undergoing large physiologic changes. Given this operating environment, it has been acceptable for these devices to have somewhat relaxed precision and accuracy requirements, given the clinical need for real-time point-of-care data for patients in critical care situations.

Both pulse oximeters and capnography instruments can be labeled as non-invasive in that neither require penetration of the outer skin or tissue to make a measurement, nor do they require a blood or serum sample from the patient to custom calibrate the instrument to each individual patient. These instruments typically have pre-selected global calibration coefficients that have been determined from clinical trial results over a large patient population, and the results represent statistical averages over such variables as patient age, sex, race, and the like.

There is, however, a growing desire within the medical community for non-invasive instruments for use in such areas as the emergency room, critical care ICU's, and trauma centers where fast and accurate data are needed for patients in potentially life threatening situations. Typically, these patients are not anesthetized and motion-induced artifacts may corrupt data from patient-attached monitoring instruments. Also, patients in shock or acute trauma may have oxygen saturation levels well below the normal physiologic range, or may suffer from reduced blood flow.

SUMMARY OF THE INVENTION

Given the situation described above there is a need for a technique to compensate for, or eliminate, motion-induced artifacts in patient-attached critical care monitoring instruments. Also, a need exists to extend the accurate operational range of patient-attached pulse oximeters in environments when the patient's blood oxygen saturation is well below the normal physiologic range, or where there is low blood flow. Consequently, the invention is directed to various approaches to improving pulse-oximetry by incorporating additional signals to aid in the triggering of the pulse-oximeter or in analyzing the data received by the pulse oximeter. These approaches include detecting when the patient moves and analyzing the pulse-oximetry data in light of the detected movement.

One particular embodiment of the invention is directed to a method of analyzing pulse oximetry measurements made on a patient. The method includes taking pulse oximetry measurements of the patient at a measurement site, detecting motion of at least a part of the patient, and analyzing pulse oximetry measurements taken at times selected according to the detected motion of the at least part of the patient.

Another embodiment of the invention is directed to a system for making a pulse oximetry measurement of a patient. The system includes means for taking pulse oximetry measurements of the patient at a measurement site, means for means for detecting motion of at least part of the patient, and means for analyzing pulse oximetry measurements taken at times selected according to the detected motion of the at least part of the patient.

Another embodiment of the invention is directed to apparatus for measuring oxygen saturation of hemoglobin at a measurement site on a patient. The apparatus includes a controller having a motion detector unit having a first input to receive an input signal related to motion of at least a part of the patient and an oxygen saturation unit having a second input to receive signals related to measurements of oxygen saturation of hemoglobin made at the measurement site. The controller analyzes signals related to measurements of oxygen saturation made at times selected based on the input signal related to the motion of the at least part of the patient.

Another embodiment of the invention is directed to a sensor unit for making measurements of hemoglobin oxygen saturation on a patient. The sensor unit includes a body attachable to the patient having one or more optical ports for delivering light to the patient at first and second wavelengths for measuring hemoglobin oxygen saturation. The body includes a motion sensor.

Another embodiment of the invention is directed to a method of analyzing pulse oximetry measurements made on a patient. The method includes taking pulse oximetry measurements of the patient at a measurement site using a pulse-oximetry sensor head. Motion of the pulse-oximetry sensor head relative to the measurement site is electronically detected.

Another embodiment of the invention is directed to a system for analyzing pulse oximetry measurements made on a patient. The system includes means for taking pulse oximetry measurements of the patient at a measurement site using a pulse-oximetry sensor head, and means for electronically detecting motion of the pulse-oximetry sensor head relative to the measurement site.

Another embodiment of the present invention is directed to a system for measuring oxygen saturation of hemoglobin at a measurement site on a patient. The system includes a controller having an oxygen saturation unit having a first input to receive signals from a pulse-oximeter sensor head. The controller also has a first motion detector analyzer having a first input to receive an input signal related to motion of at least a part of the patient, and a second motion detector analyzer having a second input to receive an input signal related to motion of the sensor head.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 9 schematically illustrates contents of data buffers used in analyzing pulse-oximetry data;

Figure 1:
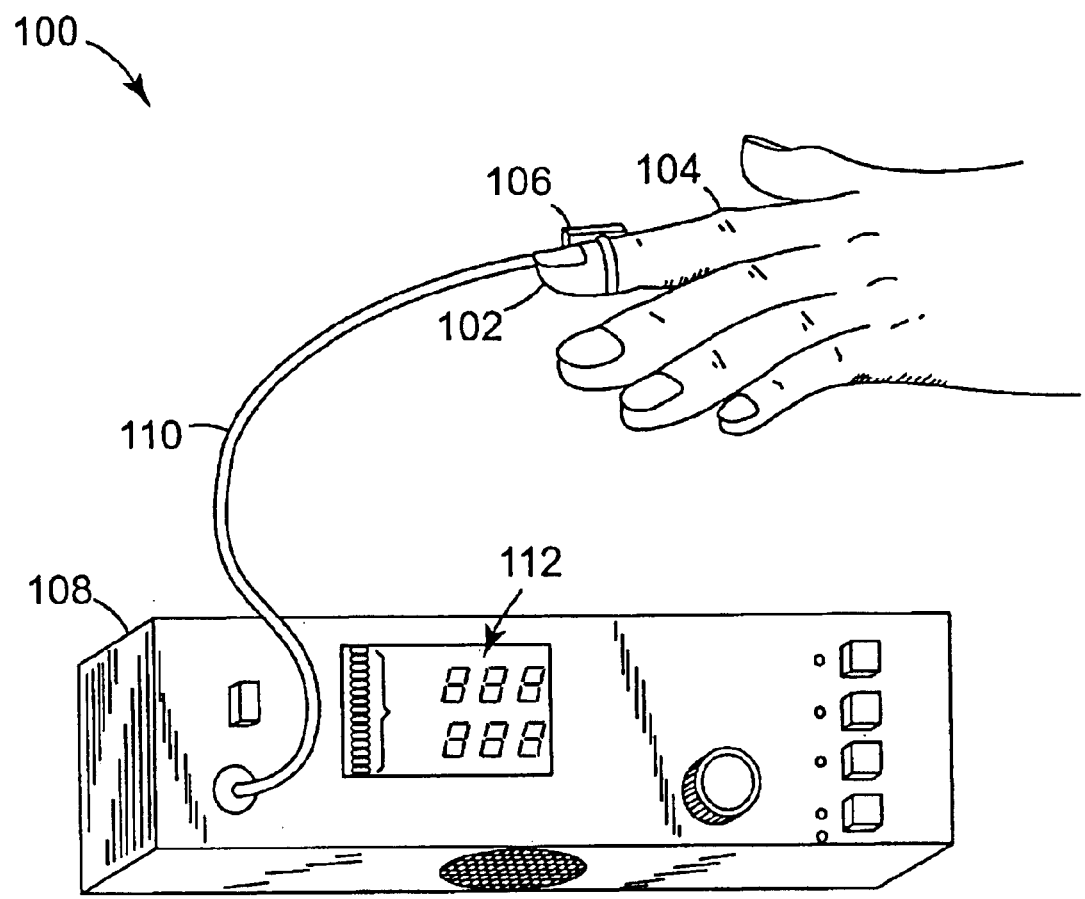
FIG. 1 illustrates a non-invasive pulse-oximetry unit attached to a patient's fingertip for the determination of blood oxygen saturation levels.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is applicable to medical devices and is believed to be particularly useful for non-invasive optical physiologic sensors.

Generally, the present invention relates to a method of measurement that augments the existing non-invasive pulse oximetry methodologies. Advanced algorithms have been developed recently for improving pulse-oximetry measurements, based on only measurements of hemoglobin oxygen saturation. The present invention is directed to the use of additional input signals, that may be used along with the new algorithms, to improve the quality of the pulse-oximetry measurement. In addition to pulse oximetry, other optical measurement techniques such as the non-invasive measurement of blood glucose can benefit from the present invention.

Pulse oximetry utilizes the pulsatile nature of blood flow to synchronize the optical measurement of oxygenated and reduced (de-oxygenated) hemoglobin. Typical commercially available pulse oximeters have two light emitting diodes (LEDs) operating at two different wavelengths, $\lambda 1$ and $\lambda 2$, one in the red region near 660 nanometers (nm) where the difference between the absorbance of oxygenated ($HbO_2$) and reduced (Hb) hemoglobin is the greatest, and a second LED in the near infrared (NIR) region. The NIR LED typically operates either near 805 nm, where the absorbance of $HbO_2$ and Hb are substantially the same (the isosbestic wavelength), or near 940 nm for increased sensitivity. An optical detector is typically mounted in a housing unit with the LEDs to detect the optical energy either transmitted through, or reflected from, the patient's tissue. Pulse oximeter sensing heads may be clipped to the patient's fingertip or the patient may insert a fingertip into a sensor housing unit. In other approaches, the pulse oximeter may be attached to the patient's head, for example the patient's ear lobe, or forehead. Use of the head for pulse oximetry measurements is advantageous because the motion of the head may be less than that of a hand, and in situations where blood flow is reduced, the flow of blood to the head may be reduced less than the flow of blood to an extremity, such as a finger. An increasingly important application for pulse-oximetry is fetal monitoring of hemoglobin oxygen saturation during childbirth. In this application, the pulse-oximeter is placed on the neonate's head.

Another location on the head where pulse oximetry measurements may be made is the buccal region (cheek), which is suitable for both reflection and transmission measurements. Making the pulse-oximetry measurement on the inside of the cheek may reduce the effects of skin color (melanin) on the measurement, particularly if the measurement is made in reflection. If the measurement is made in transmission, then the light passes through the epidermis only once, whereas reflective or transmissive measurements made on the ear lobe or finger require passage of the light through the epidermis twice, and so even transmission pulse oximetry measurements have the advantage of reduced melanin interference.

In most pulse-oximetry systems, an average over multiple blood pulses is taken to increase the signal-to-noise or signal-to-background ratio. Different approaches have been developed to synchronize the measurements to the peak and valley of the blood pulse(s) in the time domain as each individual blood pulse transits the region near the sensing LEDs and detector. In one approach, the ECG-R wave is used as a trigger to initiate a timing sequence to capture the peaks and valleys of consecutive optical pulses. If, however, the patient were to move their arm or finger during the measurement time interval, this movement, or acceleration of the arm or finger, may induce a change in the velocity of the blood entering the sensing region. This may, in turn, cause the fixed timing sequence to miss the peak of the pulsatile wave and thus corrupt the measurement process. Also, motion of the patient may result in moving the sensor relative to the skin, which distorts the measurement. Lastly, the signal to noise of the measurement decreases when the blood flow is reduced, and so it is difficult to obtain good pulse oximetry measurements under conditions of low blood flow. The following description is directed to proposed solutions to reduce motion-induced, and low flow-induced error mechanisms in pulse-oximetry systems.

A schematic representation of a pulse oximeter system 100 attached to a patient's fingertip 102 is presented in FIG. 1. The patient's hand 104 is typically not immobilized and is free to move throughout the measurement time interval. The sensor head 106 containing the LEDs and detector is attached to the patient's fingertip 102. The sensing head 106 is coupled to the main signal processing unit 108 by an interconnect 110. The interconnect 110 may be electrical or optical. The system may include a data display 112 for displaying the measured level of hemoglobin oxygen saturation, and any other information.

Some of the approaches to reducing motion-induced error include monitoring a pulsatile characteristic of the patient, such as an electroencephalographic (ECG) signal, heart beat, blood pressure, blood flow, impedance, and the like, and using this measured pulsatile characteristic either to trigger the pulse-oximeter measurements, or in the analysis of the pulse-oximeter measurements. The pulsatile characteristic of the patient may be measured using any suitable approach. For example, where the pulsatile characteristic is the heart beat, a sonometer may be used, such as a stethoscope. In other examples, blood pressure may be measured using a blood pressure cuff, blood flow velocity may be measured using laser Doppler velocimetry (LDV) and impedance may be measured using an impedance measurement system. The examples discussed below are particularly directed to the use of LDV and impedance measurements, but it will be appreciated that these are presented as examples, and that the invention is not limited to the use of LDV and impedance measurements, and may be used with other pulsatile characteristics. A particular advantage of LDV is that an LDV signal having a good signal to noise ratio may still be obtained even under conditions of low blood flow. While non-invasive measurements of pulsatile characteristics have been listed, where the measurement is made using a device that does not penetrate the patient's skin, it should be appreciated that invasive measurements of pulsatile characteristics may also be used.

It should also be noted that, although the level of hemoglobin oxygen saturation does vary over a period of a heartbeat with a pulsing variation, hemoglobin oxygen saturation is not considered to be a pulsatile characteristic, for the purposes of the present discussion.

Some pulsatile characteristics, for example, blood pressure, blood flow, and impedance, are quite different in nature from the ECG waveform. The ECG waveform is related to the electrical impulses that drive the heart beat, and originates in the central nervous system. In contrast, other pulsatile characteristics such as blood pressure, heart beat, blood flow, changing impedance and the like arise from the contraction of the heart.

Furthermore, pulse-oximetry measurements are not limited to being made on the patient's finger, but may also be made elsewhere on the patient's body. Some other suitable regions for making pulse-oximetry measurements include, but are not limited to the toe, the ear lobe, the buccal region and the sublingual region.

In one particular embodiment of the invention that uses LDV, the sensing head 106 may include elements for making make laser Doppler velocity (LDV) measurements of blood flow in substantially the same region where the pulse oximetry measurements are made. Electro-optic signal processing techniques to implement LDV measurements are described in U.S. Pat. No. 5,587,785, titled "Laser Doppler Velocimeter", by inventors Saturo Kato et. al., and also in U.S. Pat. No. 5,502,558, titled "Laser Doppler Velocimeter", by inventors James H. Menders et. al., both of which are incorporated herein by reference.

In one embodiment of an LDV-enhanced pulse oximetry system, the active electro-optics used for making LDV measurements, for example laser, detector, discrete optical components, and the like, may be housed in the pulse-oximeter main signal processing unit 108. In such a case, a fiber optic waveguide may be incorporated in the interconnect cable 110 to deliver and receive optical energy from the sensing head 106. This configuration is attractive from a commercialization viewpoint in that it does not add considerable cost to the re-usable sensor unit formed by the sensor head 106 and the interconnect cable 110. In this configuration, with the LDV sensing region/volume substantially the same as the pulse-ox sensing region/volume, the intrinsic time delay between LDV signal and the pulse-ox signal is close to zero. Accordingly, the LDV signal may be used to derive an $SaO_2$ measurement that has improved signal to noise ratio. For example, the LDV signal may be used algorithmically to anticipate and/or compensate for patient motion-induced artifacts.

Figure 2:
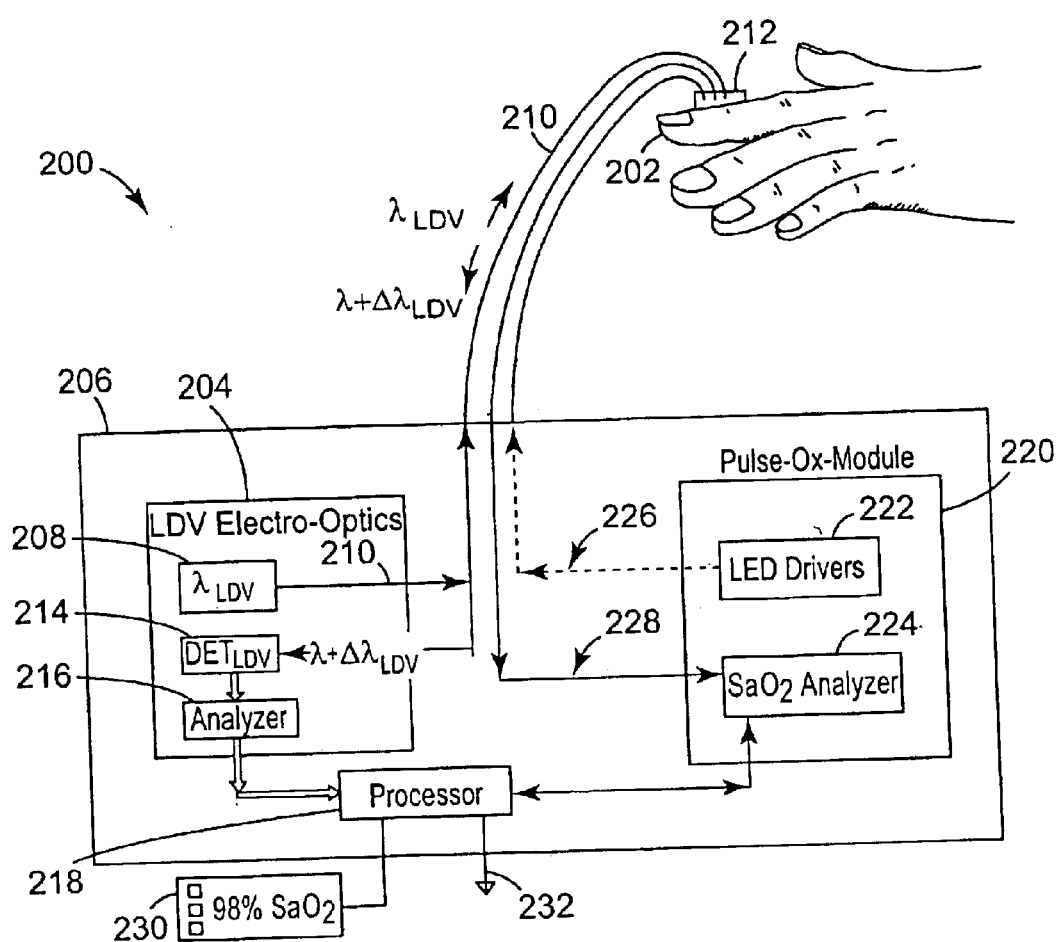
FIG. 2 shows a block schematic diagram of an enhanced pulse-oximetry unit according to an embodiment of the present invention.

A schematic representation of one embodiment of an LDV-enhanced pulse oximeter system 200 attached to a patient's fingertip 202 is presented in FIG. 2. The LDV electro-optics unit 204 may be incorporated in the main housing unit 206 of the LDV-enhanced pulse oximeter 200. The output of the LDV laser unit 208 is coupled into a fiber-optic waveguide 210, which delivers the laser energy, at a wavelength, $\lambda_{LDV}$, to the pulse-ox sensing head 212 and returns the Doppler-shifted signal, at a wavelength, $\lambda + \Delta\lambda_{LDV}$, to the LDV detector unit 214. The output of the LDV detector unit 214 is coupled to an analyzer unit 216 which may perform operations such as discrete Fourier transform analysis to determine the magnitude of the blood velocity. The analyzer unit 216 may also detect changes in velocity, in other words a concomitant acceleration component, nested in the LDV signal. The output of the analyzer unit 216 is coupled to a processor unit 218 which may generate timing signals to be used by the pulse-ox module 220.

The unit 206 may also output the results of the pulse-oximetry measurements and/or the pulsatile measurements directly, on a display 230. The displayed information may be presented digitally, for example as a series of numerical values, or may be presented graphically, for example as a function of time, or may be presented in some other manner. In addition, the system 200 may have some other type of output 232 for transferring data, including both pulse-oximetry data and LDV data. For example, the output 232 may be a parallel or serial data port for communicating with other computer equipment.

The pulse-ox module 220 may contain the electronics to generate the LED excitation signals, via the LED driver circuitry 222, and the hardware/algorithm necessary to process the returning LED signals and calculate the blood oxygen saturation, performed in the $SaO_2$ analyzer unit 224. The LED drive signals are delivered by electrical interconnect 226 to the sensor unit 212. The returning pulse-ox signal is carried by electrical interconnect 228 to the $SaO_2$ analyzer unit 224.

The pulse-ox signals received by the $SaO_2$ analyzer 224 typically show, during a heart-beat cycle, a peak absorption, corresponding to the peak flow of blood, resulting from constriction of the left ventricle, during the heart-beat cycle. At other times during the heart beat cycle, the absorption falls back to a minimum value before the next cycle starts again. The processor unit 218 may, based on the input received from the LDV unit 204, generate timing or gating pulses to synchronously detect the peaks and valleys of repetitive pulse-ox signals, which are typically used in the algorithm to calculate blood oxygen saturation.

While the processor 218 is illustrated to be separate from the LDV unit 204 and the pulse-oximeter module 220, it will be appreciated that this separation is only to show separate functions. In practice, a single microprocessor unit, or multiple microprocessors, may be used to process the data obtained via LDV and via the pulse-oximetry measurements, and to perform the function of the processor 218. This also holds for the additional embodiments of pulse-oximetry systems illustrated below.

Figure 3A:
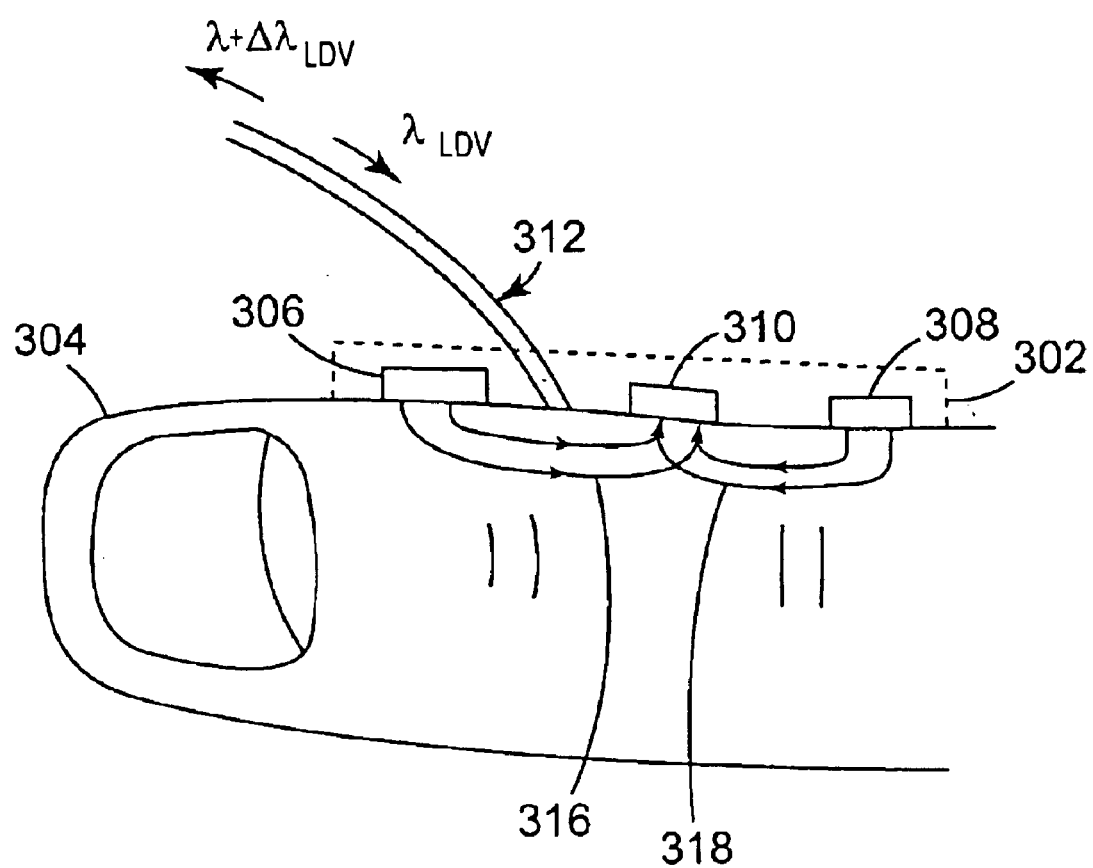
FIGS. 3A and 3B schematically illustrates cross-sectional views of pulse-oximetry sensor, that include a laser Doppler velocimetry detector, for attachment to a patient, according to embodiments of the present invention.

An expanded view of the sensing region depicting one embodiment of the sensor head unit 302 on the patient's finger 304 is schematically illustrated in FIG. 3A. The sensor head unit 302 may contain the first light source 306 and the second light source 308 and a photodetector 310, arranged so that light 316 and 318 from the light sources 306 and 308 illuminates the patient's finger 304. The light sources 306 and 308, which are typically LEDs, may straddle the detector 310 so as to be substantially equidistant from the detector 310. The light 316 at λ1 from the first source 306 passes through the patient's finger 304 to the detector 310. The light 318 at λ2 from the second light source 308 also passes through the patient's finger 304 to the detector 310, albeit along a different optical path. The time-dependent variation in the amount of light reaching the detector 310 at λ1 and λ2 is used to determine the level of oxygen saturation of the hemoglobin. It should be appreciated that hemoglobin oxygen saturation measurements may also be made with light at more than two wavelengths.

A fiber optic waveguide 312 for receiving the Doppler shifted light for the LDV measurement may be positioned proximate the detector 310 such that the LDV measurement is made in substantially the same location of the patient as the hemoglobin oxygen saturation measurements. In one embodiment, the fiber optic waveguide 312 is oriented so that the light incident on the finger from the waveguide 312 is incident on the surface of the finger 304 at an angle other than perpendicular, although the fiber optic waveguide 312 may also be oriented so that its axis is perpendicular to the finger 304. Furthermore, the light from the fiber optic waveguide 312 may be coupled directly into the patient, or through one or more optical elements, such as a lens, prism and the like. The photodetector for the LDV measurement may be positioned in the LDV module 204, in which case the fiber optic waveguide 312 forms a portion of the detector for the measurement of the pulsatile characteristic, the LDV signal.

It will be appreciated that other arrangements may also be used. For example, the pulse oximeter may, instead of locating the light sources 306 and 308 on the sensor head unit 304, include the light sources 306 and 308 in the pulse-ox module 220 itself, and may direct the light at λ1 and λ2 to the patient via one or two fiber optic waveguides. Furthermore, the detector 310 need not be placed on the surface of the patient's skin, but may be optically coupled, for example via an optical fiber, to the patient's skin.

In another embodiment, one or more of the active electro-optical components of the LDV unit 204 may be positioned at the sensor head unit 302. For example, the LDV laser unit 208 and/or the LDV detector unit 214 may be positioned on the sensor head unit 302. In another embodiment, the LDV laser unit 208 may be used to replace one of the light sources 306 and 308, so that the pulse oximetry measurements are made using light at wavelength $\lambda_{LDV}$ and at either λ1 or λ2. In such a case, $\lambda_{LDV}$ is typically selected to be at a wavelength useful for pulse oximetry measurements.

The LDV measurements need not be made in the same portion of the patient's tissue as the pulse-oximetry measurements, and the LDV measurements may also be made at a different position on the patient. For example, where the pulse-oximetry measurements are made at the a patient's digit, such as a finger or toe, the pulse oximetry measurements may be made close to the that digit, for example at another digit on the same hand or foot, on the lower limb to which the digit is attached, or to the limb to which the digit is attached. The closer the LDV measurement is made to the site of the pulse-oximetry measurement, then the smaller is the time delay between the measured pulsatile characteristic and the features of the pulse-oximetry measurement. It will be appreciated, however, that LDV measurements may be made at any position of the patient's body. These different variations just described may also be used in other embodiments discussed below.

Figure 3B:
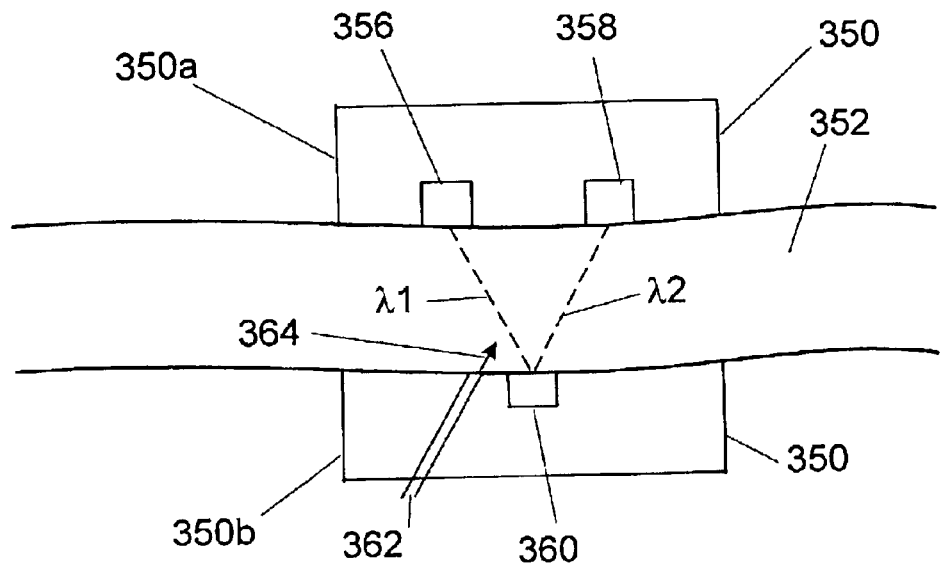

Another embodiment of a sensor head 350 that includes LDV measurement is schematically illustrated in FIG. 3B. This sensor head 350 is adapted for pulse-oximeter measurements made in transmission through the patient's tissue. Such measurements may be made at many locations of the patient including, but not limited to, a digit, the ear lobe and the cheek. Measurements of physiologic characteristics of a patient that are made at the cheek and other epithelial tissues are further discussed in U.S. patent application Ser. No.10/195,005, entitled "Method For Measuring A Physiologic Parameter Using A Preferred Site," incorporated herein by reference.

In this particular embodiment, the sensor head 350 is split into two parts that are placed on either side of a tissue flap 352, such as a digit, ear lobe, cheek or the like. The first part 350a of the sensor head 350 includes two light sources 356 and 358, operating at different wavelengths, λ1 and λ2. The second part 350b of the sensor head 350 includes a light detector 360 that detects light from the two sources 356 and 358. A fiber optic waveguide 362 is positioned on the second part 350b to direct LDV probe light 364 at a wavelength of $\lambda_{LDV}$ into the tissue flap 352, and to receive the frequency shifted light from the sampled tissue for the LDV measurement.

In another embodiment, the detector 360 may be used to detect the Doppler-scattered LDV signal light. One way of distinguishing the LDV light from the pulse-oximetry light while using a single detector 360 is to modulate the LDV light and pulse-oximetry light at different frequencies. In addition, the fiber optic waveguide 362 may be placed on the first part 350a, while the detector 360 is on the second part 350b.

Figure 4:
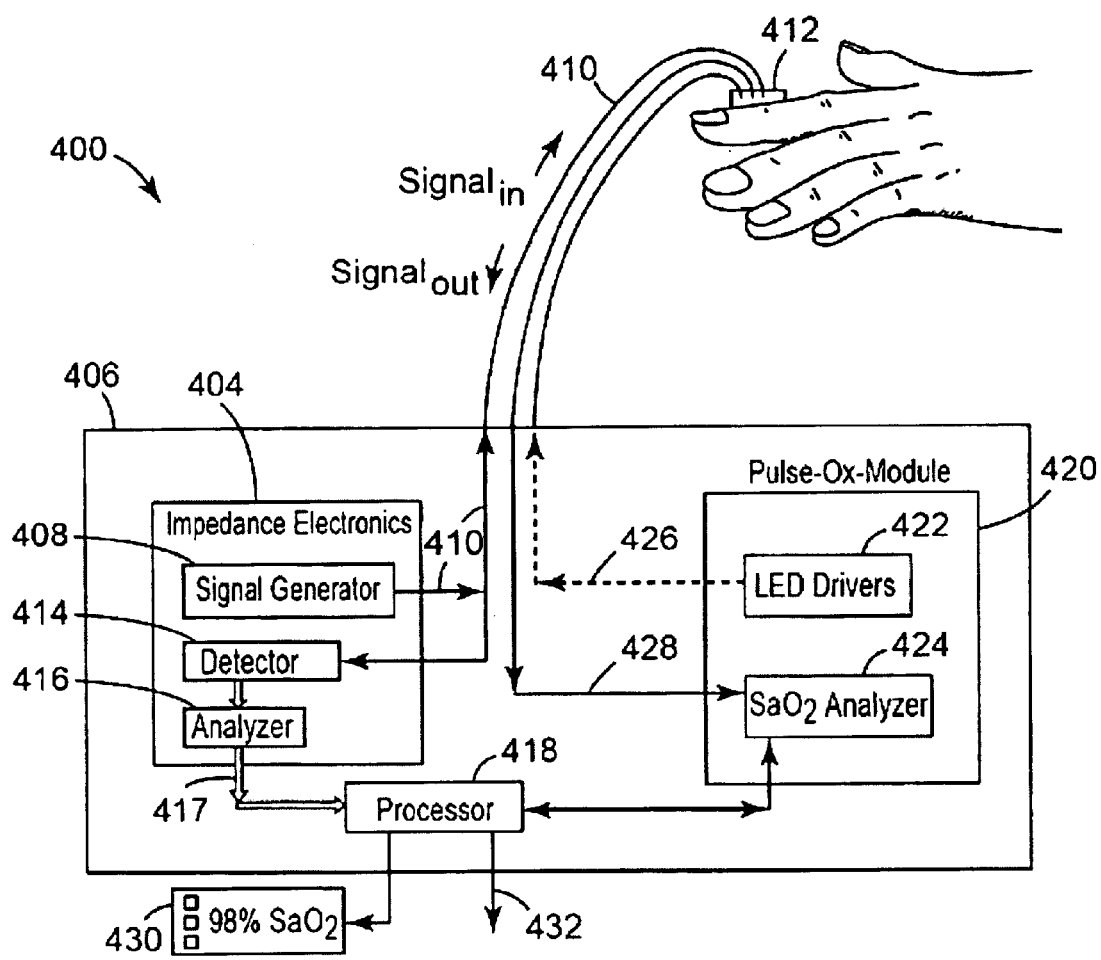
FIG. 4 shows a block schematic diagram of an enhanced pulse-oximetry unit according to another embodiment of the present invention.

A schematic representation of one embodiment of an impedance measurement-enhanced (Z-enhanced) pulse oximeter unit 400 is illustrated in FIG. 4. An impedance measurement of a patient is typically made by passing a current between two active electrodes and measuring the resulting potential difference between two passive electrodes. The measured impedance depends on the electrical conductivity of the tissue and fluid through which the current passes. The pulse of the bloodstream contributes to a pulsatile change in the amount and type of fluid in the current path, which is detected as a pulsatile change in the measured impedance.

The unit 400 includes an impedance measuring unit 404 and a pulse-oximetry module 420. The impedance measuring unit 404 may be incorporated in the main housing unit 406 of the Z-enhanced pulse oximeter 400. The impedance measuring unit 404 includes a signal generator 408 and a detector 414. Impedance measurements of a patient are typically made using a system of at least four electrodes, with the two outer electrodes being actively driven with a signal and the two inner electrodes passively receiving a signal related to the active signal and the impedance of the patient. Accordingly, the output of the signal generator unit 408 is coupled to an interconnect 410, which delivers the input signal, signal$_{in}$, to the sensing head 412, to drive the active electrodes. The interconnect 410 also returns the impedance signal, signal$_{out}$, from the passive electrodes to the impedance detector unit 414. The electrical interconnect 410 may include multiple electrical leads connecting the signal generator 408 to the pulse-ox sensing head 412, and the input and output signals from the sensing head may be on different electrical leads. An example of this type of configuration of impedance measurement is described in U.S. Pat. No. 5,178,154, titled "Impedance Cardiograph and Method of Operation Utilizing Peak Aligned Ensemble Averaging", which is incorporated herein by reference.

The output of the impedance detector unit 414 is coupled to the impedance analyzer 416 which may perform operations such as first derivative tests to determine and align repetitive peak values. The output 417 of the analyzer unit 416 may be coupled to a processor unit 418 which may then generate timing signals to be used for triggering the pulse-ox module 420. The analyzer unit 416 may also output the impedance measurements directly, so that the operator is informed of the impedance. The impedance may be presented digitally, for example as a series of numerical values, or may be presented graphically, for example as a function of time, or may be presented in some other manner.

The pulse-ox module 420 typically contains the electronics to generate the LED excitation signals, via the LED driver circuitry 422, and the hardware/algorithm necessary to process the returning LED signals and calculate the blood oxygen saturation, performed in the SaO$_2$ analyzer unit 424. The LED drive signals are delivered by electrical interconnect 426 to the sensor unit 412, and the returning pulse-ox signal is carried by electrical interconnect 428 to the SaO$_2$ analyzer unit 424. The processor unit 418 may generate timing or gating pulses to synchronously detect the peaks and valleys of repetitive pulse-ox signals, corresponding to positions of maximum and minimum light absorption by the blood, and which are typically used in the algorithm to calculate blood oxygen saturation. The processor unit 418 may use any appropriate approach for analyzing the incoming impedance data. For example, the impedance data may be subject to a fast Fourier transform, a discrete Fourier transform, or to other transform or filtering methods. Several approaches are available for using the analyzed impedance signal to improve the signal to noise of the results of the pulse oximetry measurements. Some of these approaches are taught by analogy in U.S. Pat. No. 5,178,154. The unit 400 may include a display 430 for displaying pulse-oximetry results to the operator. The display 230 may also display the measured pulsatile characteristic, in this case the impedance. The information may be presented digitally, for example as a series of numerical values, or may be presented graphically, for example as a function of time, or may be presented in some other manner. In addition, the system 400 may have some other type of output 432 for transferring data, including both pulse-oximetry data and the pulsatile data. For example, the output 232 may be a parallel or serial data port for communicating with other computer equipment. An expanded view of the sensing region depicting one particular embodiment of the sensor head unit 502 on the surface of the patient's finger 504 is schematically illustrated in FIG. 5. The sensor head unit 502 may contain the first light source 506 and the second light source 508, which may be LEDs. The light sources 506 and 508 may straddle the detector 510 so as to be substantially equidistant from the detector 510.

In this particular embodiment, the impedance measurement technique is carried out using a pair of active electrodes 512 and 514, and a pair of passive electrodes 516 and 518. The electrodes 512 and 514 contact the patient's finger 504 to provide a current stimulus to the finger 504. The current flowing between electrodes 512 and 514 develops a voltage drop which can be measured between electrodes 516 and 518, the voltage being a product of the current and the tissue and/or blood impedance. The voltage measured between electrodes 516 and 518 may then be detected by the detector 414 and analyzed in the analyzer 416.

In the illustrated configuration, the impedance measurement may be made in substantially the same physical location as the pulse-ox measurement. Also, in this configuration the impedance signal typically contains a pulsatile component synchronous with the arrival of blood pulses. In such a case, the measured impedance signal may be used as a trigger to initiate pulse-ox measurements, to ensure that the pulse-ox measurements are made synchronously with the flow of blood in the patient.

Figure 5B:
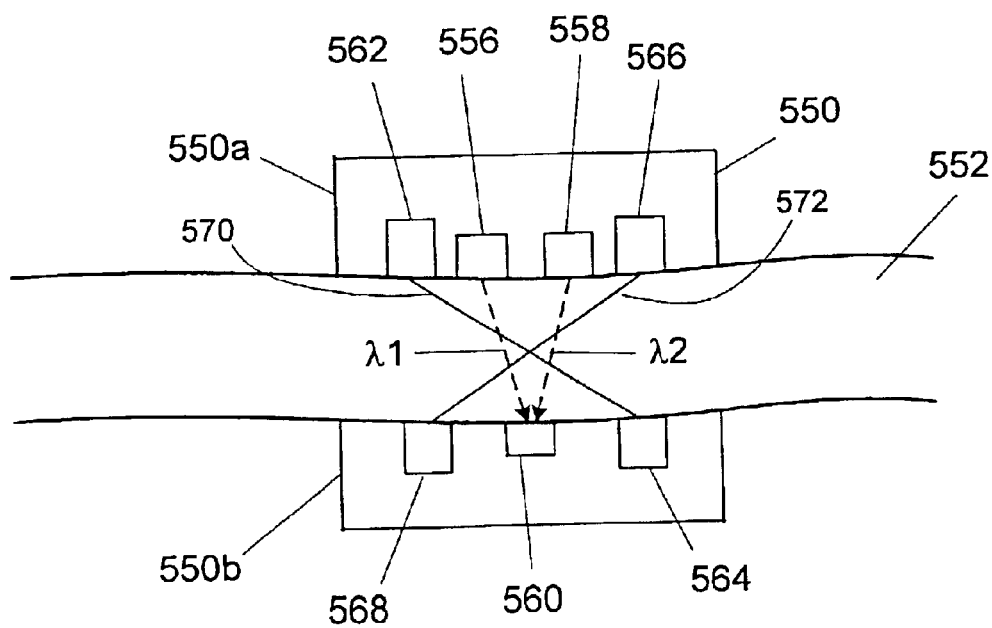
FIGS. 5A and 5B schematically illustrate cross-sectional views of pulse-oximetry sensors, that include impedance sensors, for attachment to a patient, according to other embodiments of the present invention.
Figure 5A:
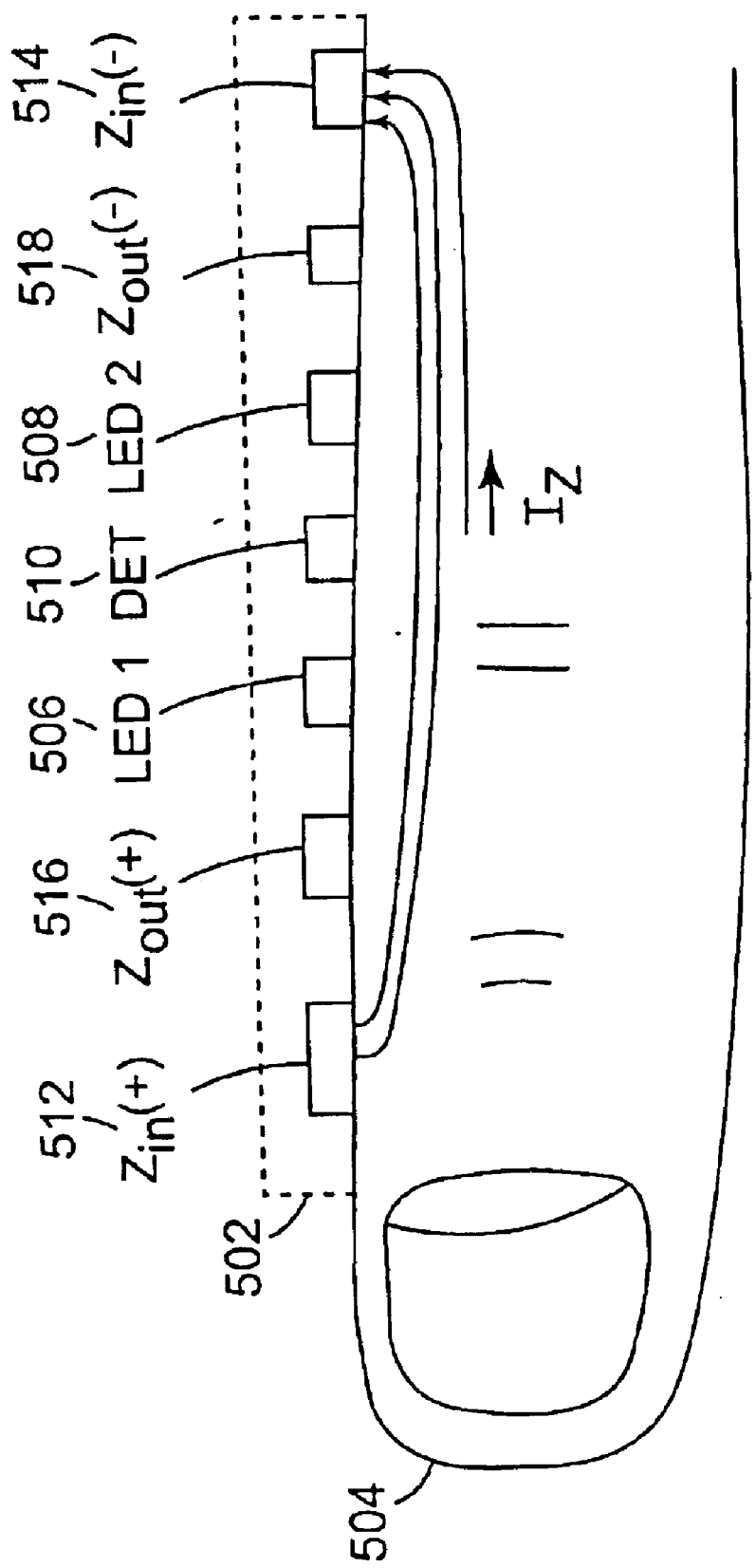

Another embodiment of a sensor head 550 that includes impedance measurement is schematically illustrated in FIG. 5B. This sensor head 550 is adapted for pulse-oximeter measurements made in transmission through the patient's tissue. Such measurements may be made at many locations of the patient including, but not limited to, a digit, the ear lobe and the cheek. Measurements of physiologic characteristics of a patient that are made at the cheek and other epithelial tissues are further discussed in U.S. patent application Ser. No. 10/195,005, entitled "Method For Measuring A Physiologic Parameter Using A Preferred Site."

In this particular embodiment, the sensor head 550 is split into two parts that are placed on either side of a tissue flap 552, such as a digit, ear lobe, cheek or the like. The first part 550a of the sensor head 550 includes two light sources 556 and 558, operating at different wavelengths, λ1 and λ2. The second part 550b of the sensor head 550 includes a light detector 560 that detects light from the two sources 556 and 558. The sensor head 550 also includes first and second active electrodes 562 and 564 for applying a current to the tissue flap 552, and two passive electrodes 566 and 568 for measuring a potential difference that arises due to the current passing between the active electrodes 562 and 564.

In this particular embodiment, the electrodes are positioned such that the current path 570 between the active electrodes 562 and 564 passes through the region sampled by the pulse-oximetry light sources 556 and 558. Furthermore, a line 572 drawn between the passive electrodes 566 and 568 crosses current path 570.

Figure 7:
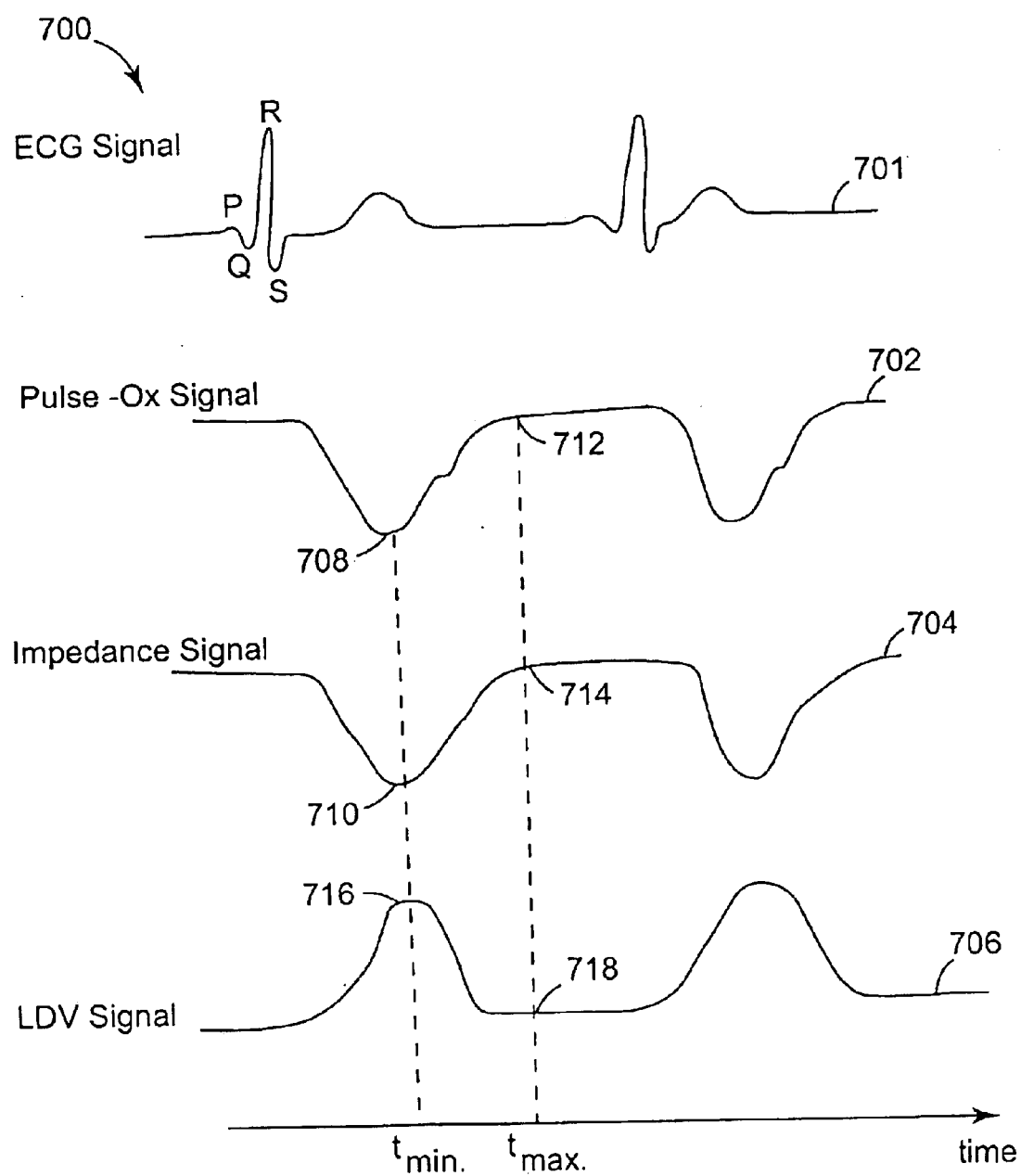
FIG. 7 schematically shows the temporal dependence of pulse-oximeter signals, impedance signals and laser Doppler velocimetry signals.

A timing diagram 700 is presented in FIG. 7, showing the relative timing between an ECG signal 701, a pulse-oximeter signal 702, an impedance signal 704, and an LDV signal 706. In this case, the impedance and LDV signals are assumed to have been made proximate the pulse-oximeter measurement site, for example as shown in FIGS. 3 and 5, so that there is little relative delay between the impedance or LDV measurements and the change in light absorption resulting from the pulse of blood passing the measurement site.

In this configuration, the minima of the pulse-oximetry signal 708, corresponding to increased optical absorption in the blood may occur at substantially the same time ($t_{min}$) as the minima 710 of the impedance signal 704, where the minima in both signals may represent the arrival of a blood pulse. Likewise, the minimum in 708 the pulse-oximeter signal 702 substantially coincides with the maximum 716 in the LDV signal 706, corresponding to maximum blood flow velocity.

Also, the maxima 712 of the pulse-oximetry signal 702 may occur at substantially the same time ($t_{max}$) as the maxima 714 of the impedance signal 704, and the minima 718 of the LDV signal 706. Accordingly, the impedance signal 704 and/or the LDV signal 706 may be used as a trigger for collecting pulse-oximetry data. Where the LDV or impedance measurement are made proximate the measurement site for the pulse-oximetry measurements, the timing between the impedance and/or LDV measurement and the pulse-oximetry signal does not significantly change, even if the patient moves. Accordingly, the light sources of the pulse-oximeter may be triggered to pulse at around $t_{min}$ and $t_{max}$, in which case the noise of the ensemble average should be reduced.

In another approach, illustrated in FIG. 9, pulse-oximetry data are received as a train of sampled data representing a sampling of the pulse-oximeter signal 702. The data are stored in a buffer, with an associated time stamp. The pulse-oximetry data are represented as $POD_i$, where the subscript "i" is an integer, while the time stamp data are represented by $t_i$. Data from a pulsatile measurement, such as an LDV measurement or impedance measurement, represented as $PMD_j$, are also stored, along with associated time stamps, represented by $tt_j$. A selected value of $PMD_j$, $PMD_{jmax}$, that represents a predetermined value for which it is known that the associated blood absorption value is a maximum, is selected. The value of $POD_{imax}$, whose time stamp, $t_{imax}$, is closest to $tt_{jmax}$, may then be selected as the value of PMD that represents the maximum value of the blood absorption. Similarly, the time $tt_{jmin}$, that represents a predetermined time for which it is known that the associated blood absorption is at a minimum may then be selected, and the value of $POD_{imin}$, whose time stamp, $t_{imin}$, is closest to $tt_{jmin}$, may be selected as the value of PMD that represents the minimum value of blood absorption. The hemoglobin oxygen saturation may then be calculated using $PMD_{imax}$ and $PMD_{imin}$.

As indicated above, impedance and LDV signals are examples of pulsatile patient characteristics that may be used to enhance pulse-oximetry measurements. Pulsatile characteristics that may be used fall into two broad categories. One is pulsatile characteristics that result from contraction of the heart, such as blood pressure and acoustic heart beat signal and the like. This category also includes impedance and LDV characteristics. The other category is pulsatile characteristics that do not result from contraction of the heart. An example of this type of characteristics is an ECG signal.

The device used for measuring the pulsatile characteristic may be placed proximate the site where the pulse-oximetry measurement is made. Here, the term "proximate" is intended to cover positions not only near the measurement site, but also at the measurement site. Advantages provided by proximate measurement of the pulsatile characteristic include that the relative timing between the pulse-oximetry measurement and the pulsatile characteristic is less sensitive to patient motion. Accordingly, the improvement in pulse oximetry signal to noise that results from including the pulsatile characteristic is also less sensitive to patient motion. Additionally, the combination of different types of sources, detectors and other components into a single sensor head may lead to overall reduction in the cost of manufacturing an improved pulse-oximeter system.

In other embodiments, the pulsatile characteristic may be measured at some location removed from the pulse-oximetry measurement site. For example, impedance measurements made on the patient's torso may be used in conjunction with pulse-oximetry measurements made on the patient's digit. It will be appreciated that the further removed the pulsatile measurement is from the pulse-oximetry measurement site, the larger the delay may be between the timing of the pulsatile characteristic and the timing of the change in optical absorption detected in the pulse-oximetry measurements. Measurements made at one position on the patient may be less sensitive to motion artifacts than at others.

A problem with using an ECG signal as a pulsatile characteristic is that ECG monitoring typically involves the placement of several electrodes widely spaced across the patient's torso. The measurement of pulsatile characteristics arising from contraction of the heart, on the other hand, may be measured using a single sensor, or a set of closely spaced sensors on a single housing attached to the patient. Furthermore, the patient may have a heart condition in which the stimulus to the heart is faulty. Use of a pulsatile characteristic arising from contraction of the heart avoids problems arising from a faulty stimulus, or from a heart that responds to the stimulus in an abnormal way. Since the goal of the pulse oximetry measurement is to measure a quantity affected by the flow of blood around the body it is, therefore, advantageous to use as additional signals other inputs that are directly related to the flow of blood around the body.

Figure 10:
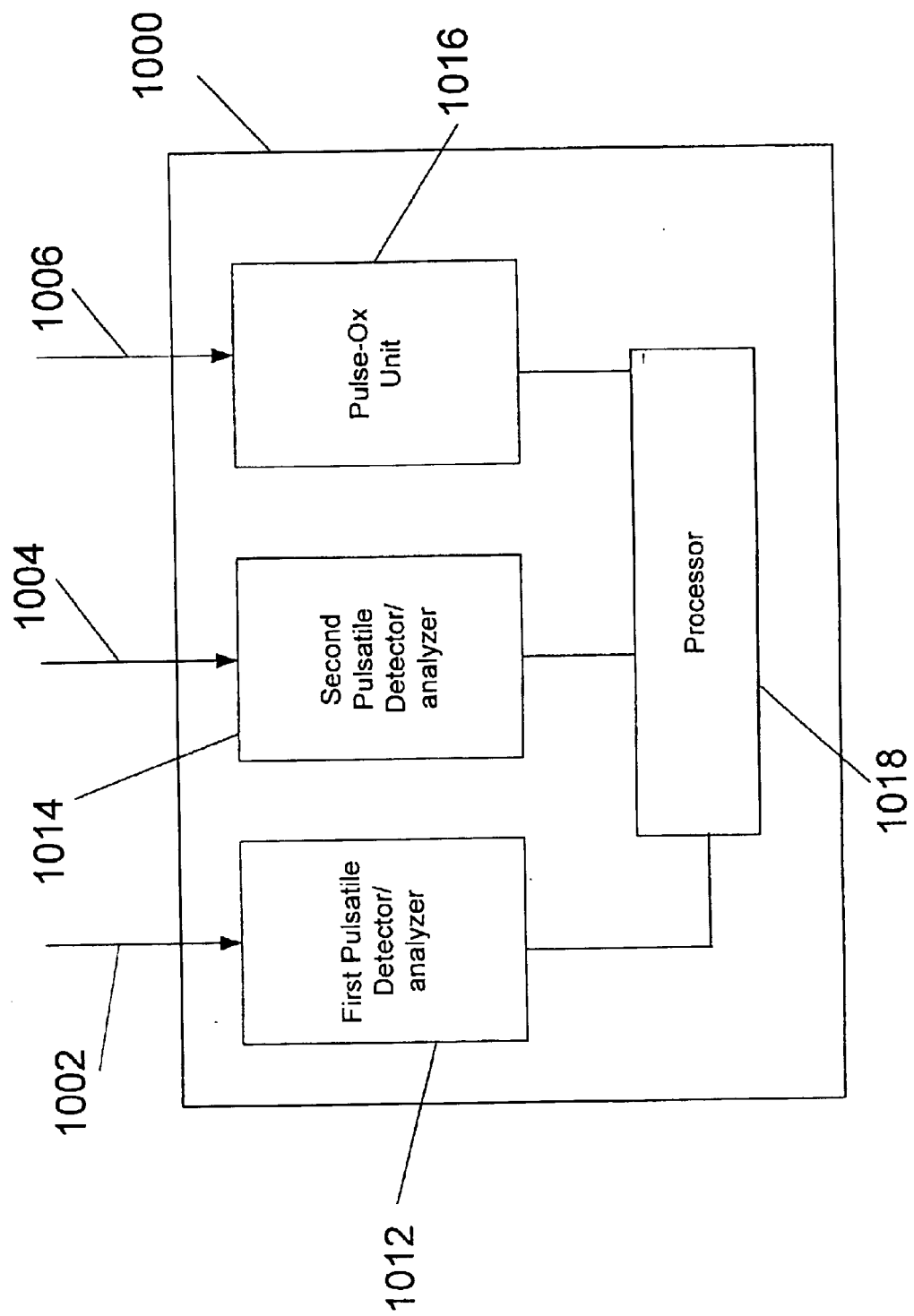
FIG. 10 schematically illustrates an embodiment of a pulse-oximetry system that includes inputs for two pulsatile characteristics, in addition to the pulse-oximetry measurements, according to an embodiment of the present invention.

In another embodiment of the invention, the pulse-oximetry unit may include the input of two or more pulsatile signals to aid in the generation of the measurement of hemoglobin oxygen saturation. One embodiment of such a system 1000 is schematically illustrated in FIG. 10. For example, the unit 1000 may include two inputs 1002 and 1004 for pulsatile signals that result from contraction of the heart, in addition to an input 1006 for receiving pulse-oximetry data. In such a case, the first input signal may be detected and/or analyzed by a first detector/analyzer 1012 and the second input signal may be detected and/or analyzed by a second detector/analyzer 1014. The pulse oximetry measurements received at the third input 1006 may be detected and/or analyzed in the pulse oximeter unit 1016. The pulsatile signals applied to the two inputs 1002 and 1004 may be associated with different types of pulsatile characteristic, or may be associated with the same type of characteristic. Furthermore, the signals applied to the two inputs 1002 and 1004 may be made at the same position on the patient, or at different positions. To illustrate, the signals applied to the inputs 1002 and 1004 may both be LDV signals, measured at the same position on the patient or at different places.

The processor 1018, in addition to performing the functions discussed above with regard to triggering the pulse oximetry measurement and analyzing the pulse oximetry data, may also perform various checks or confirm operations to determine that the pulsatile data received are useful For example, the processor 1018 may compare the data received at the two inputs 1002 and 1004 to determine whether there is an expected correspondence between the two measurements of pulsatile characteristics. The processor 1018 may then determine whether to use either of the measured pulsatile signals to trigger the pulse oximeter unit 1016 or to otherwise aid in the analysis of the pulse oximeter measurements. The processor 1018 may also determine a signal to noise level for each of the measured pulsatile signals and use that measured pulsatile signal having the more useful signal to noise level for triggering the pulse oximeter measurements or otherwise aiding in the analysis of the pulse oximeter measurements.

The unit 1000 may output measured pulse-oximetry and pulsatile results on a display (not shown) or may transmit measurement data to other equipment on some other type of output (not shown).

One of the inputs 1002 and 1004 may also include an ECG measurement or other pulsatile characteristic that is not generated by contraction of the heart. It may be useful to compare a pulsatile characteristic generated by contraction of the heart with, for example, an ECG signal as a control to ensure that the pulsatile characteristic generated by contraction of the heart corresponds in some manner to the ECG signal. For example, one test may be to ensure that the pulsatile characteristic resulting from contraction of the heart occurs at a rate equal to the rate of the ECG signal. An event where the rates change or where the relative phasing between the two signals changes may be indicative of a change in status of the patient, and may even be sufficient reason for setting an alarm. In addition, a change in the relative nature of the two pulsatile signals may be used to indicate a failed measurement of one of the two pulsatile signals.

Another factor that may affect the usefulness of the pulse-oximetry measurement is the motion of the patient while the measurement is taking place. In particular, motion of the patient, for example that part of the patient where the pulse-oximetry measurements are being made, may result in the change of timing between any trigger for the pulse-ox measurements and the absorption extrema in the pulse-oximetry measurements. For example, if a virtual trigger is used to set the window for pulse-oximetry measurements that relates to a single heart beat, movement of the patient may result in the absorption maximum in the pulse-oximetry measurement moving around within that window. This relative time shift of the pulse-oximetry measurement as a result of patient movement is particularly of concern when the motion is large, random, and/or violent, for example when the patient is in shock, is shivering, or is having a seizure.

Figure 6:
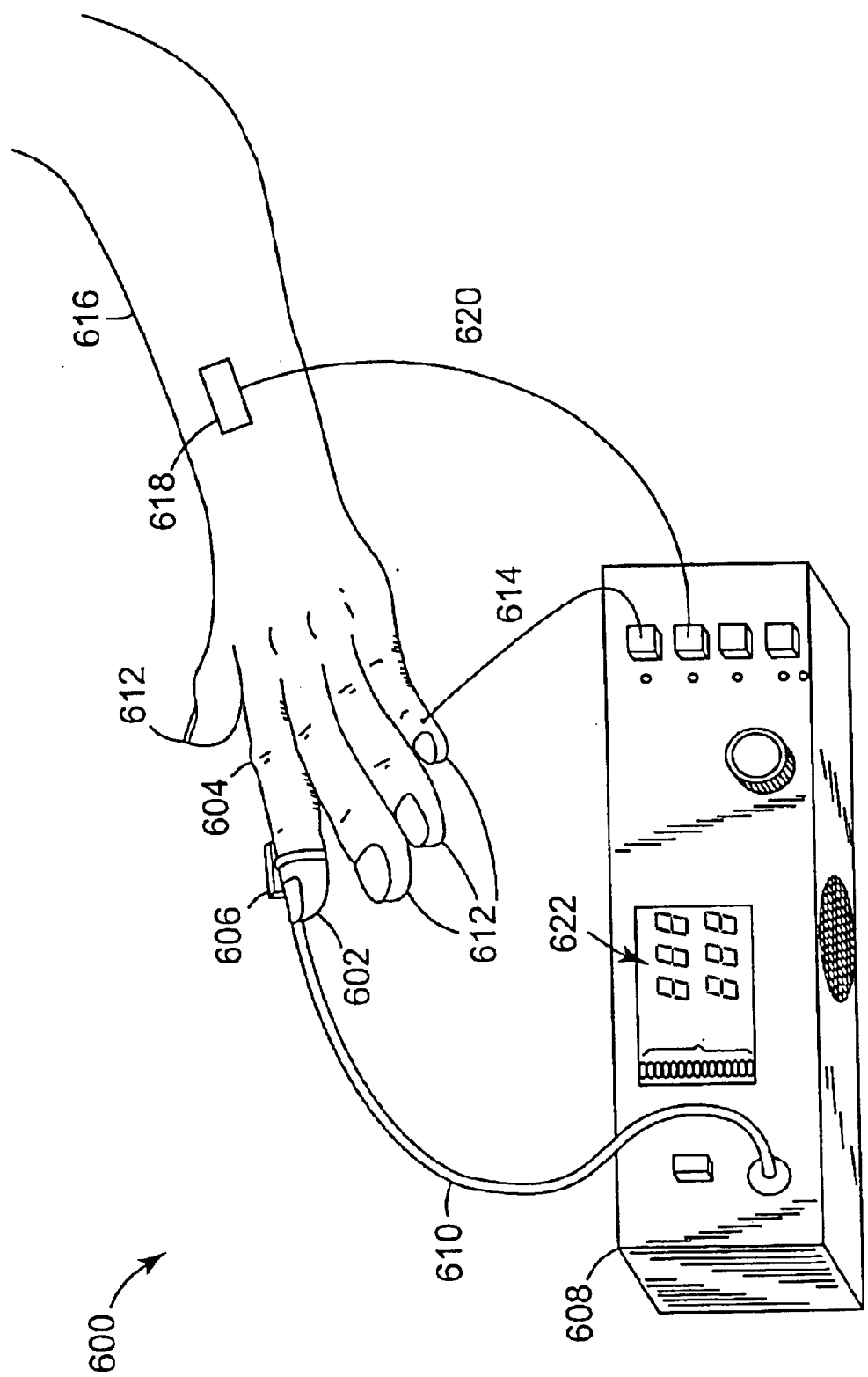
FIG. 6 schematically illustrates a non-invasive pulse-oximetry unit that incorporates motion detection, according to an embodiment of the present invention.

One particular example of a pulse-oximeter system 600 that may be useful in reducing the problems associated with patient motion is schematically represented in FIG. 6. In this embodiment, a pulse-oximeter sensor unit 606 is attached to the patient's fingertip 602. The patient's hand 604 is not immobilized and is free to move while the pulse-oximetry measurements are being made. The sensor head 606 containing the LED's and detector is attached to the patient's fingertip 602. The sensing head 606 is attached to the main signal processing unit 608 by an interconnect 610.

In one embodiment of the present invention, the sensing head 606 may incorporate a motion sensor, such as a linear accelerometer, which may sense erratic motion, periodic motion (such as tapping), or even violent motion of the sensing head 606. Such motions may interfere with the normal operation of the pulse-oximetry system. Where the detected motion lies above a particular threshold, for example in the case of extreme or violent motion of the sensing head 606, the signal from the motion sensor may be used to generate a blanking command in the main signal processing unit 608 to disregard data collected during those incidents. Conversely, during periods where the sensing head 606 is stationary, the signal from the motion sensor may be used as a gating command to validate raw data as acceptable for downstream processing. In another approach, the main signal processing unit may be programmed to not take pulse-oximetry data while the motion sensor detects motion that exceeds a particular threshold. In one embodiment of an accelerometer, the motion sensor is a small piezo-electric device commercially available from multiple vendors, e.g., National Instruments Inc., Austin, Tex.

In another embodiment of the present invention, the motion sensor may be mounted on the patient's adjacent fingertip(s) 612 and may be coupled to the main signal processing unit 608 via electrical interconnect 614. In another embodiment, the motion sensor 618 may be mounted elsewhere on the patient, for example on the patient's forearm 616. The separately-mounted sensor 618 may be coupled to the main signal processing unit 608 via an electrical interconnect 620. The unit display 622 may indicate that the patient's movement has exceeded a certain threshold and, for example, may be sufficient to adversely affect the pulse-oximetry measurement.

Figure 11:
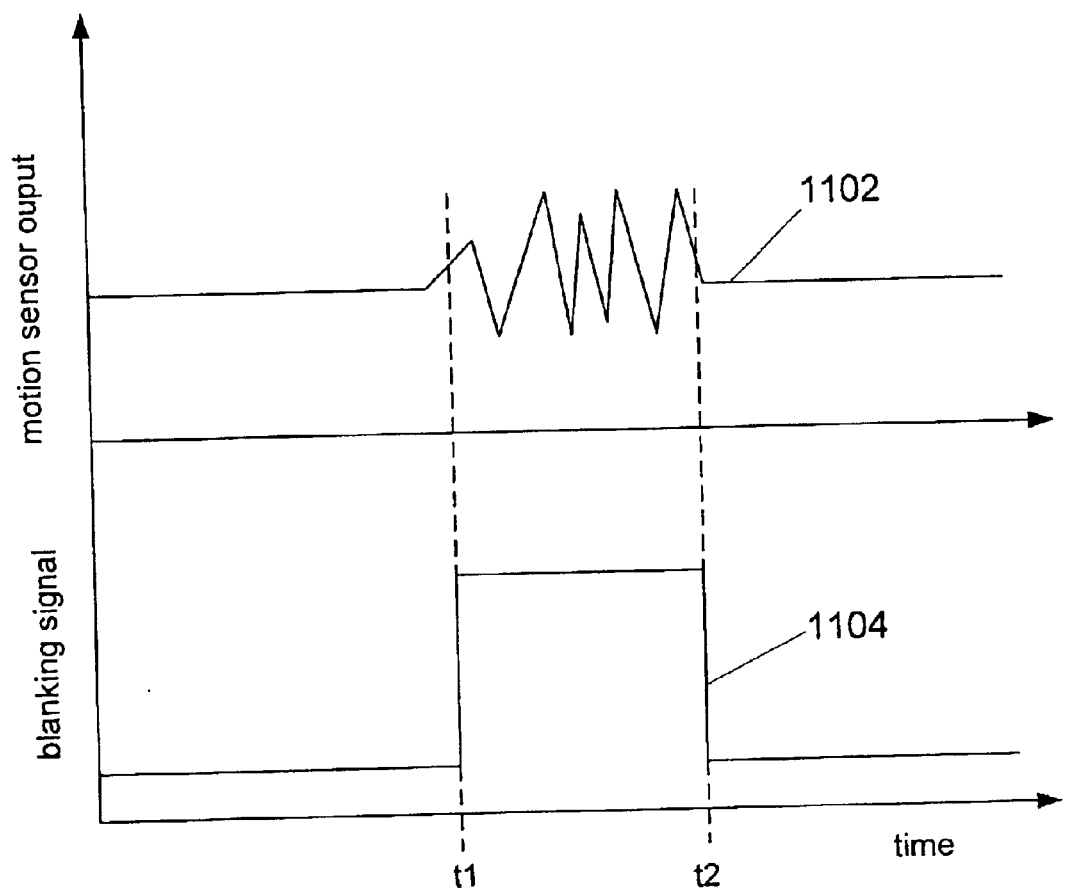
FIG. 11 schematically shows timing diagrams for motion detection and the generation of a motion detection signal according to an embodiment of the present invention.

FIG. 11 shows two curves showing the relative timing of a blanking signal and a motion signal. Curve 1102 is an example of the output from the motion sensor, showing relative calm before time t1 and after t2. In the period between t1 and t2, however, the patient is moving, as is reflected in the motion sensor output. The pulse-oximeter system may generate a blanking signal 1104 related to the detected motion. For example, the blanking signal may turn on when the motion is detected to be above a certain threshold, and may stay on if the motion exceeds that threshold within a certain period of time following previous excursion beyond that threshold. The blanking signal 1104 may also be set according to different motion criteria.

The blanking signal 1104 may be used for any process used in analyzing the data that is related to the patient's motion. For example, the blanking data may be used to tag data taken during periods of motion deemed to be too excessive to make accurate pulse-oximetry readings, so those data taken during periods of excessive motion may be ignored when producing a pulse-oximetry result. The motion signal 1102 may also otherwise aid in making a pulse-oximetry measurement. For example, the unit may analyze the motion signal 1102 to determine the frequency or frequencies of the patient's motion and then, when analyzing the pulse-oximetry data, may filter out those artifacts having a frequency or frequencies corresponding to the motion frequencies.

Figure 8:
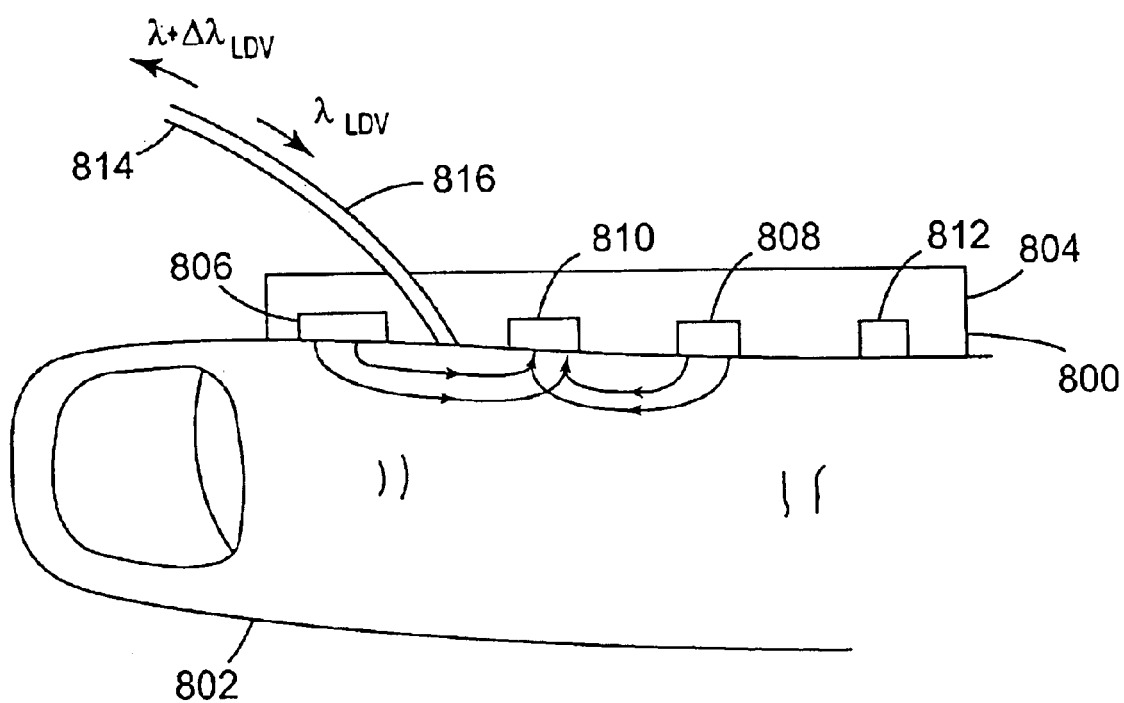
FIG. 8 schematically illustrates a pulse-oximeter sensor head that includes a detector for detecting patient motion, according to an embodiment of the present invention.

An embodiment of a sensor head 800 attachable to the patient, for example at the patient's finger 802, is schematically illustrated in FIG. 8. The sensor head 800 has a body 804 that includes first and second light sources 806 and 808 for directing light into the patient at two different wavelengths and a photodetector 810 for detecting the light signals. The light sources 806 and 808 and the photodetector 810 may be used for making measurements of the hemoglobin oxygen concentration. The sensor head 800 also as a motion sensor 812 that may be integrated with the body 804. The motion sensor 812 may be coupled to the pulse-oximeter controller to provide information regarding patient motion. The sensor head 800 may also include at least part of sensor 814 for measuring a pulsatile characteristic of the patient. In the illustrated example, the pulsatile sensor 814 includes a fiber 816 for receiving an LDV signal from the patient. The fiber 816 may also direct the LDV probe light to the patient.

It may be useful to determine when the pulse-oximeter sensor unit has moved relative to the patient. This may happen, for example if the sensor head slips relative to the patient's skin if the patient is moving violently.

An approach for permitting such determinations to be made includes the use of two motion sensors, one on the sensor head and one on the patient: the detection of a change in the difference between the signals of the two motion sensors may permit determination that the pulse-oximetry sensor head has moved. Once such a determination has been made, the system may then use this information in the analysis of the pulse-oximetry measurements.

Figure 12:
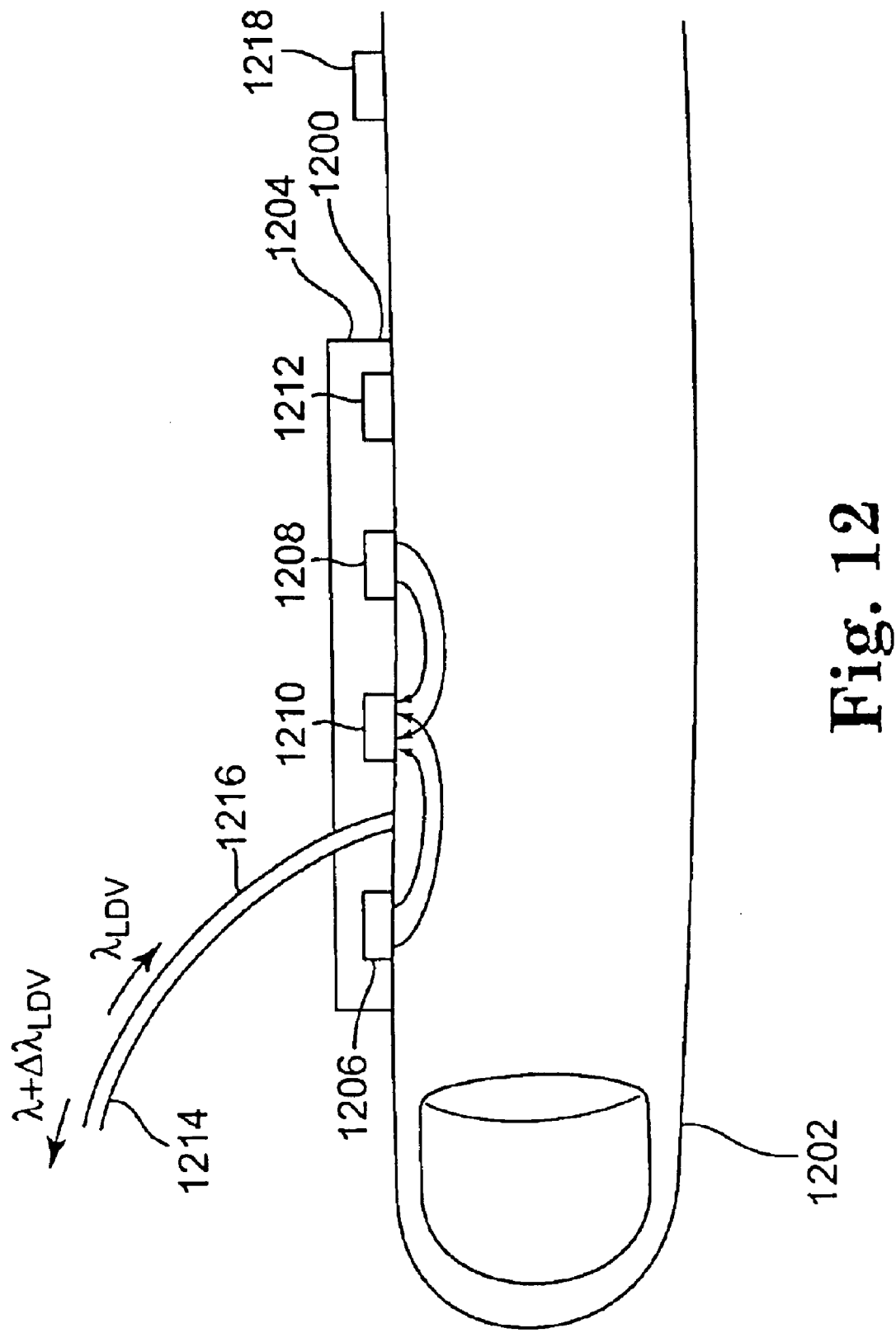
FIG. 12 schematically illustrates a pulse-oximeter sensor head arrangement that includes two detectors for detecting patient motion, according to an embodiment of the invention.

One example of a multiple motion sensor arrangement on a patient is schematically illustrated in FIG. 12. A sensor head 1200, attachable to the patient, for example at the patient's finger 1202, has a body 1204 that includes first and second light sources 1206 and 1208 and a detector 1210 for making pulse-oximetry measurements. The sensor head 1200 also as a motion sensor 1212 that may be integrated with the body 1204. The motion sensor 1212 may be coupled to the pulse-oximeter controller to provide information regarding patient motion. The sensor head 1200 may also include at least part of sensor 1214 for measuring a pulsatile characteristic of the patient. In the illustrated example, the pulsatile sensor 1214 includes a fiber 1216 for receiving an LDV signal from the patient. The fiber 1216 may also direct the LDV probe light to the patient. The at least part of a sensor may also be used to detect other types of pulsatile characteristic.

Exterior to the sensor head 1200, a second motion sensor 1218 may be attached to the patient in a location near sensor head 1200, for example on the same finger. In this embodiment, the motion signals from the two motion sensors 1212 and 1218 are tracked, and any differences in the signals may be used to determine if the sensor head 1200 has slipped relative to the patient, or even has become dislodged. Accordingly, it is preferred for the second motion sensor 1218 to be mounted close to the first motion sensor 1212.

Figure 13:
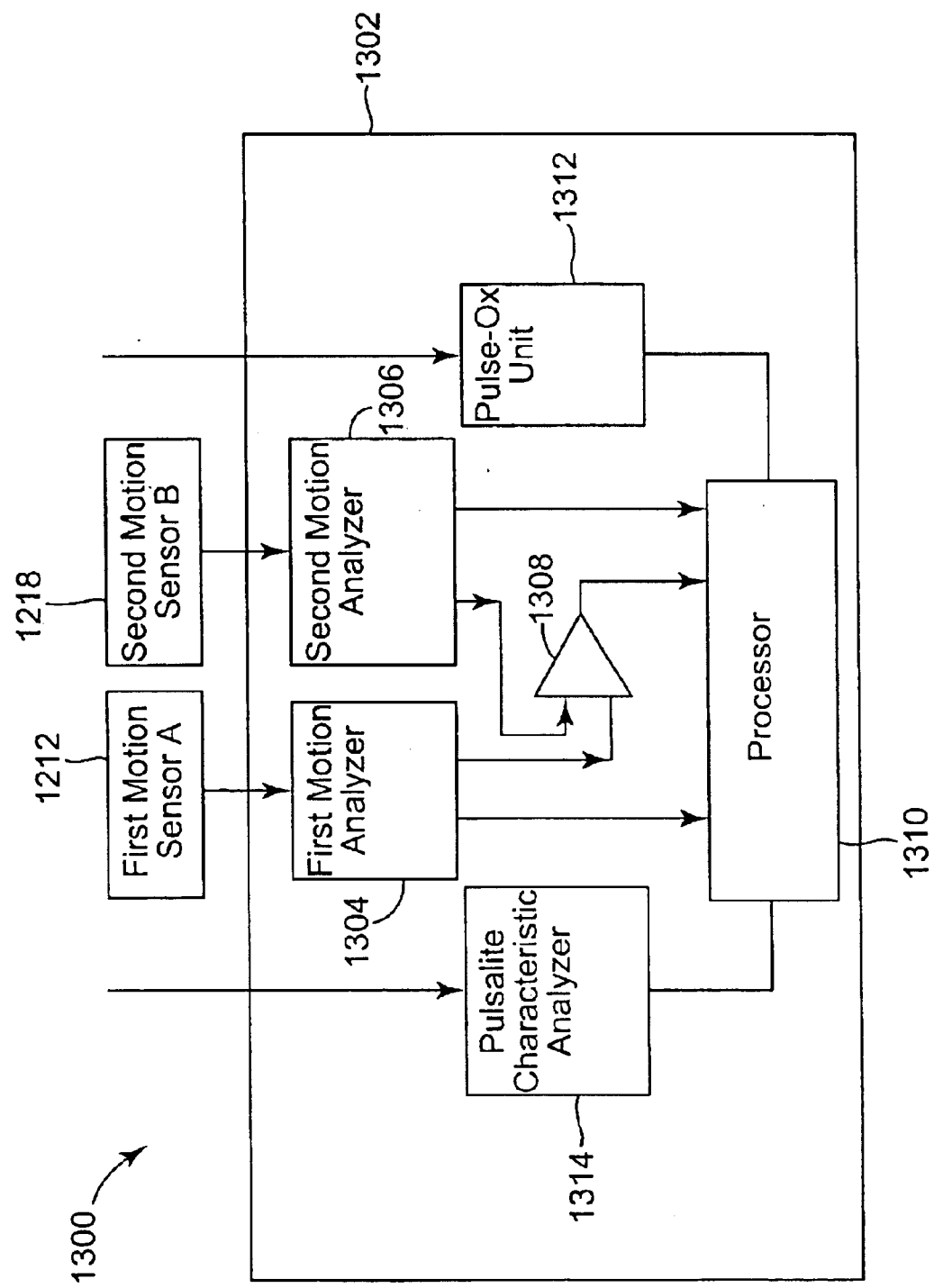
FIG. 13 schematically illustrates an embodiment of a pulse-oximeter system that includes inputs for two motion signals, in addition to the pulse oximetry signals, according to an embodiment of the invention.

One particular embodiment of a system that uses inputs from multiple motion sensors is schematically illustrated in FIG. 13. The system 1300 includes a controller 1302 that has first and second motion sensor analyzers 1304 and 1306 to analyze the signals from the first and second motion sensors 1212 and 1218 respectively. A differentiator 1308 may be used to produce a differential signal based on the first and second motion signals. Any changes in the differential signal may be caused by movement of the sensor head 1200 relative to the patient, for example the sensor head 1200 may slip or become dislodged.

The processor 1310 may be connected to receive the differential signal in addition to output signals form the first and second motion analyzers 1304 and 1306. The processor 1310 may activate an alarm, for example a visual or acoustic alarm, in response to a detected motion of the sensor head 1200 relative to the patient. In addition, the manner in which the processor 1310 processes pulse-oximetry data obtained by the pulse-oximetry unit 1312 may change depending on the differential signal. For example, pulse-oximetry data having a time stamp close to a motion event signaled by the differential signal may be ignored when performing an ensemble average. In another approach, the pulse-oximetry data obtained prior to such a motion event may be ignored when performing an ensemble average, so that the average is made only over measurements taken at one particular sensor position on the patient.

The controller 1302 may also include one or more analyzers 1314 for analyzing measurements of one or more pulsatile characteristics of the patient.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

I claim:

1. A method of analyzing pulse oximetry measurements made on a patient, comprising:

taking pulse oximetry measurements of the patient at a measurement site with a first device;

detecting motion of at least a part of the patient with a second device separate from the first device; and analyzing pulse oximetry measurements taken at times selected according to the detected motion of the at least part of the patient, wherein detecting the motion of at least a part of a patient includes receiving motion signals from at least two different parts of the patient.

2. A method as recited in claim 1, wherein taking pulse oximetry measurements includes measuring absorption of light at at least first and second wavelengths in the patient.

3. A method as recited in claim 1, wherein detecting the motion of the at least part of the patient includes measuring acceleration of the at least part of the patient.

4. A method as recited in claim 1, wherein detecting the motion of the at least part of the patient includes measuring motion of the patient at the measurement site.

5. A method as recited in claim 1, wherein detecting the motion of the at least part of the patient includes measuring motion of the patient at a part of the patient different from the measurement site.

6. A method as recited in claim 1, wherein taking pulse oximetry measurements includes taking pulse oximetry measurements on a patient's digit.

7. A method as recited in claim 1, further comprising determining when the at least part of the patient is not moving, based on the detected motion of the at least part of the patient, and taking pulse oximetry measurements only at a time when the at least part of the patient is determined to be not moving.

8. A method as recited in claim 7, wherein analyzing the pulse oximetry measurements includes analyzing the pulse oximetry measurements made when the at least part of the patient is determined to be not moving.

9. A method as recited in claim 1, further comprising measuring a pulsatile characteristic of the patient, wherein at least one of i) taking the pulse oximetry measurements of the patient and ii) analyzing the pulse oximetry measurements is performed in response to the measured pulsatile characteristic.

10. A method as recited in claim 1, further comprising generating a patient motion signal based on the detected motion of the at least part of the patient and wherein analyzing the pulse oximetry measurements includes determining whether to accept or reject the pulse oximetry measurements based on the patient motion signal, and analyzing accepted pulse oximetry measurements.

11. A method of analyzing pulse oximetry measurements made on a patient, comprising:
taking pulse oximetry measurements of the patient at a measurement site with a first device;
detecting motion of at least a part of the patient with a second device separate from the first device; and
analyzing pulse oximetry measurements taken at times selected according to the detected motion of the at least part of the patient,
wherein taking pulse oximetry measurements includes taking pulse oximetry measurements on a patient's digit and detecting motion of at least a part of the patient includes receiving motion signals from the digit and the limb to which the digit is attached.

12. An apparatus for measuring oxygen saturation of hemoglobin at a measurement site on a patient, comprising:
a controller having:
a motion detector unit for receiving an input signal related to motion of at least a part of the patient; and
an oxygen saturation unit for receiving signals related to measurements of oxygen saturation of hemoglobin made at the measurement site;
a sensor head attachable to the patient at the measurement site for making hemoglobin oxygen saturation measurements, the sensor head being coupled to the oxygen saturation unit; and
a sensor coupled to the motion detector unit, the sensor being separate from the sensor head, so as to permit motion sensing of a portion of the patient different from the measurement site;
wherein the controller analyzes signals related to measurements of oxygen saturation made at times selected based on the input signal related to the motion of the at least part of the patient; and
wherein the sensor head includes an additional sensor to detect motion, the additional sensor being coupled to the motion detector unit.

13. An apparatus as recited in claim 12, wherein the sensor is an accelerometer to detect motion of the patient.

14. An apparatus as recited in claim 12, wherein the controller determines when the at least part of the patient is moving, based on the input signal related to the motion of the at least part of the patient, and makes no measurements related to hemoglobin oxygen saturation when the patient is moving at a level beyond a selected threshold.

15. An apparatus as recited in claim 12, wherein the controller receives and stores signals related to hemoglobin oxygen saturation from the patient, determines when the at least part of the patient is not moving based on the input signal related to the motion of the at least part of the patient, and analyzes signals associated with times when the patient is determined not to be moving.

16. An apparatus as recited in claim 12, wherein the controller receives signals related to hemoglobin oxygen saturation from the patient, determines when the at least part of the patient is not moving based on the input signal related to the motion of the at least part of the patient, and analyzes signals associated with times when the patient is determined not to be moving.

17. An apparatus as recited in claim 12, wherein the controller includes an input to receive a pulsatile input signal related to a pulsatile characteristic of the patient and the controller analyzes signals related to measurements of oxygen saturation or triggers measurements of oxygen saturation based on the pulsatile input signal.

18. A method of analyzing pulse oximetry measurements made on a patient, comprising:
taking pulse oximetry measurements of the patient at a measurement site using a pulse-oximetry sensor head; and
detecting motion of the pulse-oximetry sensor head relative to the measurement site;
wherein the pulse-oximetry sensor head remains attached to the patient after moving relative to the measurement site; and
wherein detecting motion of the pulse-oximetry head includes detecting motion of the sensor head and detecting motion of a portion of the patient proximate the sensor head and determining that the pulse-oximetry head has moved relative to the measurement site based on a difference between the detected motion of the sensor head and the detected motion of the portion of the patient.

19. A method as recited in claim 18, further comprising generating an alarm after detecting the motion of the sensor head relative to the measurement site.

20. A method as recited in claim 18, further comprising generating a relative motion signal after detecting the motion of the sensor head relative to the measurement site and analyzing pulse-oximetry measurement data in response to the relative motion signal.

21. A method as recited in claim 20, wherein analyzing the pulse-oximetry measurement data includes flagging data taken at a time associated with the motion of the sensor head relative to the measurement site.

22. A method as recited in claim 18, further comprising measuring a pulsatile characteristic of the patient and analyzing the pulse oximetry measurements, wherein at least one of i) taking the pulse oximetry measurements and ii) analyzing the pulse oximetry measurements is performed in response to the measured pulsatile characteristic.

23. A method of analyzing pulse oximetry measurements made on a patient, comprising:
taking pulse oximetry measurements of the patient at a measurement site using a pulse-oximetry sensor head;
detecting motion of the pulse-oximetry sensor head relative to the measurement site;
generating a relative motion signal after detecting the motion of the sensor head relative to the measurement site; and
analyzing pulse-oximetry measurement data in resgonse to the relative motion signal;
wherein analyzing the pulse-oximetry measurement data includes ensemble averaging data taken only after a time associated with the motion of the sensor head relative to the measurement site.

24. A system for measuring oxygen saturation of hemoglobin at a measurement site on a patient, comprising:
a controller having
an oxygen saturation unit having a first input to receive signals from a pulse-oximeter sensor head,
a first motion detector analyzer having a first input to receive an input signal related to motion of at least a part of the patient; and
a second motion detector analyzer having a second input to receive an input signal related to motion of the sensor head.

25. A system as recited in claim 24, further comprising a differentiator unit coupled to receive signals from the first and second motion detector analyzers and to produce a differential output signal.

26. A system as recited in claim 24, further comprising a processor coupled to receive a differential signal based on a difference between the input signal related to motion of at least a part of the patient and input signal related to motion of the sensor head.

27. A system as recited in claim 26, wherein the processor analyzes pulse-oximetry data based on the differential signal.

28. A system as recited in claim 26, wherein the processor signals an alarm based on the differential signal.

29. A system as recited in claim 24, controller further comprising a pulsatile input to receive a signal related to a pulsatile characteristic of the patient and comprising a processor, the processor at least one of i) controlling the oxygen saturation unit and ii) analyzing pulse oximetry data in response to the pulsatile input.

* * * * *